United States Patent
Frey et al.

(10) Patent No.: US 7,404,931 B2
(45) Date of Patent: Jul. 29, 2008

(54) DEVICE FOR SEPARATING AND DISCHARGING PLASMA

(75) Inventors: Guenter Frey, Ellerstadt (DE); Norbert Ladiges, Bruehl (DE); Siegfried Noetzel, Wilhelmsfeld (DE); Bernd Roesicke, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 688 days.

(21) Appl. No.: 10/705,713

(22) Filed: Nov. 10, 2003

(65) Prior Publication Data

US 2004/0222168 A1 Nov. 11, 2004

(30) Foreign Application Priority Data

Nov. 11, 2002 (DE) .................. 102 52 223

(51) Int. Cl.
*B01D 63/00* (2006.01)
*B01D 61/00* (2006.01)

(52) U.S. Cl. .............. 422/101; 210/645; 210/650; 436/177; 436/178

(58) Field of Classification Search ........ 422/101; 210/645, 650; 436/177, 178
See application file for complete search history.

(56) References Cited

U.S. PATENT DOCUMENTS

| | | | | |
|---|---|---|---|---|
| 3,596,652 A | * | 8/1971 | Winkelman | ............. 600/575 |
| 3,791,933 A | | 2/1974 | Moyer et al. | ............. 195/127 |
| 3,832,969 A | * | 9/1974 | Rapoza et al. | ............. 283/81 |
| 3,897,340 A | * | 7/1975 | Ayres | ............. 210/314 |
| 4,226,713 A | * | 10/1980 | Goldberg | ............. 436/71 |
| 4,477,575 A | | 10/1984 | Vogel et al. | ............. 436/170 |
| 4,883,764 A | * | 11/1989 | Kloepfer | ............. 436/63 |
| 5,130,231 A | | 7/1992 | Adams et al. | |
| 5,364,533 A | * | 11/1994 | Ogura et al. | ............. 210/645 |
| 5,922,210 A | * | 7/1999 | Brody et al. | ............. 210/767 |
| 2002/0143298 A1 | * | 10/2002 | Marsden | ............. 604/190 |

FOREIGN PATENT DOCUMENTS

| | | |
|---|---|---|
| DE | 3130749 A1 | 2/1983 |
| DE | 196 29 656 | 1/1998 |
| EP | 0747105 A2 | 12/1996 |
| EP | 0785012 A1 | 7/1997 |

* cited by examiner

*Primary Examiner*—Jill Warden
*Assistant Examiner*—Paul S Hyun

(57) ABSTRACT

The invention concerns plasma separation on a microliter scale. The method/system according to the invention is able to provide plasma in the range of several microliters within a very short time as it is required, for example, in modern analyses by carrier-bound test elements. Plasma separation and plasma release is carried out in two separate consecutive steps of the method using the device according to the invention such that hemolysis during plasma separation can be avoided despite an accelerated procedure. The device comprises a disposable unit in which the device is characterized by an economical and simple method of production.

15 Claims, 3 Drawing Sheets

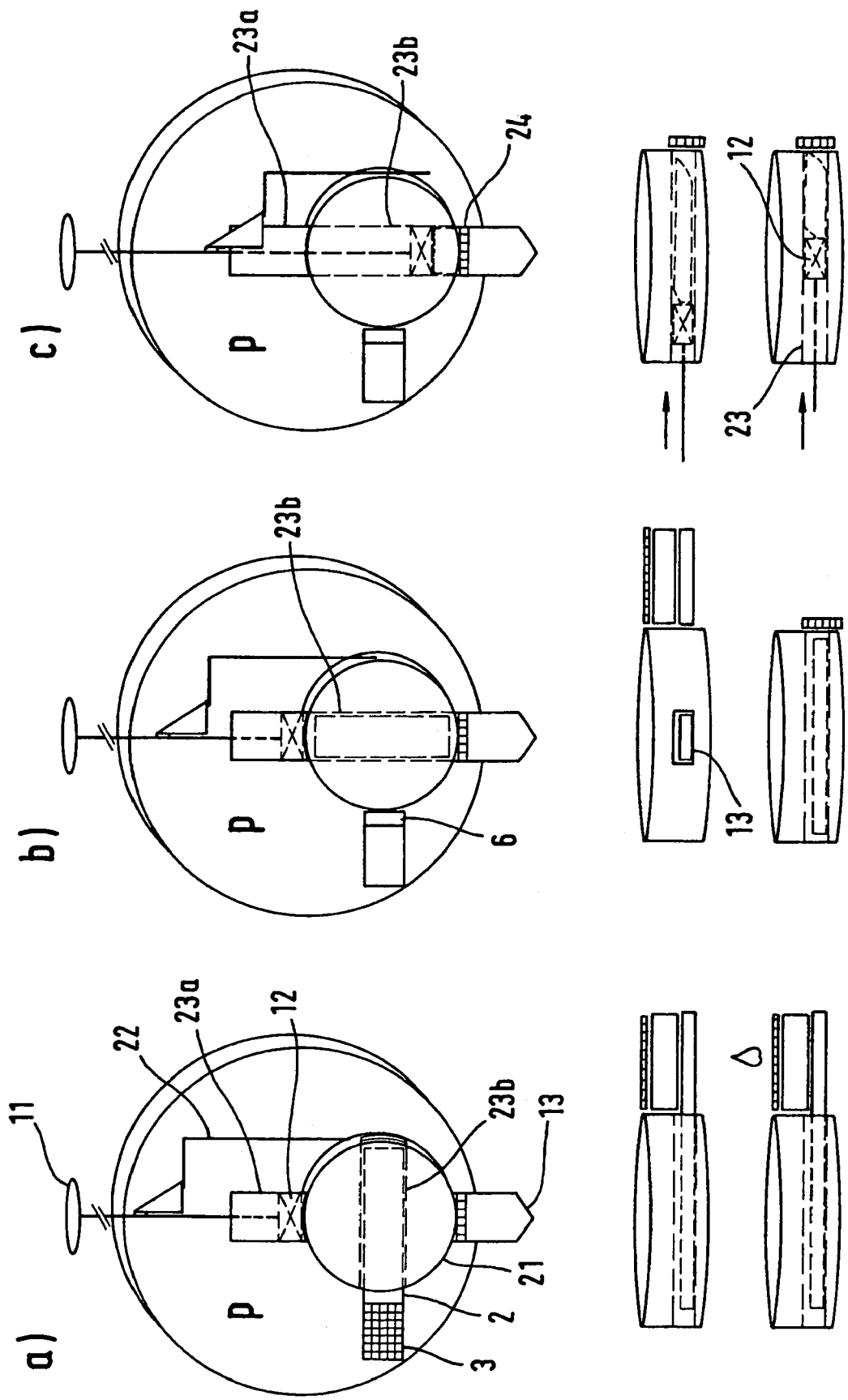

DEVICE FOR SEPARATING AND DISCHARGING PLASMA

BACKGROUND OF THE INVENTION

The present invention relates to plasma collection and, more particularly, to a device and method for separating and discharging plasma. The field of plasma collection plays an important role in analytical methods for determining a concentration of blood components. In many cases such blood tests cannot be carried out with whole blood since this contains corpuscular components (blood cells) which could result in an interference of the assay procedure. Hence, in order to carry out many analytical methods it is necessary to firstly isolate plasma from whole blood, which plasma should be as free as possible from cellular material.

A conventional method for isolating plasma for blood tests is the centrifugation procedure in which cellular components of the blood are separated on the basis of centrifugal forces. This method is laborious and is especially unsuitable when only small amounts of plasma are required for an analysis. However, particularly modem miniaturized tests use quantities of plasma that are only in the range of a few microliters. This applies especially to so-called carrier-bound tests in which an analytical system that is as small and compatible as possible is present, for example, in the form of a test strip. In this case all reagents and other agents required to carry out the test are integrated into the test strip. In order to determine an analyte the sample liquid is contacted with such an analytical element. The reagent contained in the test element reacts within a short period with the analyte to be determined such that a physically detectable change occurs on the analytical element. Such a change can, for example, be a colour change or a change in a measurable electrical variable. The change is measured and calculated with the aid of an evaluation instrument in order to output an analytical result.

An example of an analytical system which determines an analyte from plasma by means of such a test element is the HDL test (high density lipoproteins). The determination of the HDL concentration in blood is, among other things, important for the risk assessment of coronary heart disease and is thus in recent times used to diagnose one of the most common modem diseases.

The severity of a coronary heart disease can be assessed on the basis of several known parameters such as total cholesterol, in the blood, plasma or serum. Since the concentration of total cholesterol is of only limited use for individual risk assessment, the low density lipoproteins (LDL) and the high density lipoproteins (HDL) are quantified separately from one another in modern analytical methods. When assessing such analytical methods it must be taken into account that there is a positive correlation between LDL cholesterol and a coronary heart disease but a negative correlation between HDL cholesterol and the disease. Clinical studies have proven that, as a first approximation, the determination of HDL and total cholesterol is sufficient for a risk assessment. This is the preferred method in current diagnostic practice.

HDL cholesterol is, for example, determined by means of an analytical element such as those known in the prior art (e.g., HDL test elements from Roche Diagnostics GmbH). Since the HDL cholesterol is determined separately, the other lipoprotein classes that are present have to be separated from the remaining blood components to allow the determination of HDL cholesterol in plasma. Such a test, for example, requires a plasma volume of about 40 µl in order that the concentration can be determined independently of the applied plasma volume. Only pure plasma in which there are substantially no blood components can be used to determine HDL cholesterol. A complexing agent which is also integrated into the test element is additionally used to determine the HDL concentration. Plasma is then applied to the zone of the test element in which the complexing agent is present. The complexing agent EDTA is, for example, used in the prior art to analyze HDL cholesterol.

However, an analyte in pure plasma can also be determined by means of a test element that requires no complexing agent to determine an analyte. Such test elements are, for example, used to determine enzymes and are described in the prior art in the document DE 3130749 among others. Test elements which determine an analyte in pure plasma but do not contain a complexing agent are often designed such that the test element itself separates plasma. For this purpose such test elements contain a separation layer in addition to a reagent layer. In order to measure an analyte whole blood is firstly applied to the separation layer. Blood components are separated from the plasma within the separation layer and the plasma is passed on to the reagent layer. In this manner an analyte can be determined in pure plasma although blood has been applied to the test element. However, such a plasma separation layer integrated into the test element cannot be used when using complexing agents. If a complexing agent is used to determine an analyte, it turns out that the complexing agent in the test element prevents the separation of plasma from blood. Hence, the test element can no longer separate plasma if the test element contains a complexing agent.

Since, on the one hand, a complexing agent is needed to determine HDL cholesterol by one of the test elements described above and, on the other hand, it is necessary to separate plasma from blood, it follows that the plasma has to be already separated from blood on a µl scale before applying blood to the test element.

In this connection the determination of HDL cholesterol is only one important example of an analyte determination which requires small amounts of pure plasma for analysis. Other fields of application for the use of released plasma are in the field of clinical analysis. Since test strips are currently preferably used in diagnostic practice as analytical systems, there is an increasing need for simple methods for obtaining small amounts of plasma in order to achieve an overall simplification and more rapid analytical procedure.

In this respect several methods have been described in the prior art which are intended to simplify the isolation of small amounts of plasma. The aim is to obtain plasma from likewise small volumes of blood to spare the patients a laborious blood withdrawal which would, for example, be required for a centrifugation method.

Filtration methods in which different filter media and in particular membrane and glass filters are used have been discussed for many years and in some cases have been used successfully. Earlier examples of filtration technology are described in U.S. Pat. Nos. 3,791,933 and 4,477,575. A recent example comprising a complicated combination of membrane and glass filters is described in U.S. Pat. No. 5,922,210. Small amounts of plasma are obtained by microfiltration with the aid of a microcomponent. The blood cells are separated by a so-called barrier channel which is too small to allow blood cells to flow through the barrier channel. However, manufacture of a device with such a channel requires special manufacturing processes which are complicated. The said plasma collection methods have the additional disadvantage that there is a high risk of the fine pores being clogged up by mechanical plugging or by accumulation of cellular material on the walls of the pores. This would reduce the filter capacity. However, an enlargement of the filter capacity would require more space for the filter medium. This would in turn have an unfavorable effect in relation to the applied sample volume and volume of plasma obtained.

A filtering process for collecting plasma is described in U.S. Pat. No. 4,477,575 which comprises a glass fiber layer which improves the relation between sample volume and the volume of plasma obtained. In this case the volume of plasma to be separated is preferably less than 30% of the suction volume of the glass fiber layer. The filtering process takes place after blood has been applied to the glass fiber layer and is driven solely by gravity and hence the plasma isolation is correspondingly time consuming.

In order to accelerate plasma collection other methods for collecting plasma have been described in the prior art. In the patent application EP 747105 a glass fiber onto which blood is applied is firstly stored in a vessel. Pressure is exerted by a plunger on the glass fiber and the blood contained therein to accelerate the filtration process. The blood is thus pressed through the glass fiber resulting in a separation of plasma from other blood components. The plasma is discharged via an outlet. However, a disadvantage of the described device is that large amounts of blood sample are required due to the filtering process. In addition, pressing out the glass fibers results in a destruction of the corpuscular blood components and hence it is not possible to obtain pure plasma.

A vessel for plasma collection, which is described in the patent application EP 0 785 012, is based on a similar principle. In this case pressure is also exerted on a filter material to which blood has previously been applied to allow plasma separation to occur. As already described above, the pressing out process destroys blood cells and hence pure plasma is not obtained. Once plasma has been contaminated by the destruction of blood cells, it is unsuitable for use in numerous analytical tests.

SUMMARY OF THE INVENTION

It is against the above background that the present invention provides certain unobvious advantages and advancements over the prior art. In particular, the inventors have recognized a need for improvements in devices and methods for separating and discharging plasma.

Although the present invention is not limited to specific advantages or functionality, it is noted that the device and method allows plasma that is as pure as possible to be obtained on a µL scale from whole blood.

In accordance with one embodiment of the present invention, a device for separating and discharging plasma is provided. The device comprises a separation element comprising a first zone on which blood is applied. Corpuscular blood components are substantially completely retained in the first zone of the separation element whereas plasma is passed into a second zone of the separation element, typically by means of capillary forces. The separation element is configured such that the first zone of the separation element is accessible to the user for blood application. The device also has a discharge unit which, after plasma separation, acts on the second zone of the separation element without having an effect on the first zone of the separation element that would, for example, lead to blood hemolysis. If the discharge units acts exclusively on the second zone of the separation element, the separated plasma is released from the second zone and discharged through an outlet of the device.

In accordance with another embodiment of the present invention, a system for detecting analytes in blood is provided. In addition to the device according to the present invention, the system, as already described, also comprises a test element which enables detection of an analyte in plasma when the plasma separated by the device is applied.

The device according to the present invention ensures an effective collection of plasma on a µl scale even from small sample volumes. For example, plasma volumes of 30 µl or more can be obtained from 100 µl blood. Hence, the device according to the present invention is particularly suitable for the field of modem analyses since it already enables a rapid plasma separation and discharge of the plasma onto a test strip even when only small volumes of sample are drawn. If the applied blood volume is typically 30 to 150 µl, the device according to the present invention can be used to obtain sufficient amounts of plasma that are specified for commercial test elements in order that an analyte concentration can be determined independently of the applied sample volume. Consequently, the device according to the present invention enables sufficiently large amounts of plasma to be obtained despite small blood volumes in order to meet the requirements of commercial analytical methods especially with test elements.

Furthermore, the device according to the present invention allows a particularly simple and cost-effective manufacture of the system since, for example, small microstructures (microchannels) do not have to be integrated into the device in the manufacturing process. The plasma is separated by means of a separation element that is typically designed for single use. Thus, a blockage of the microporous structures due to multiple use and contamination can be avoided.

The present invention can also provide for the release of the plasma and the separation of the plasma from blood, which according to the invention, are carried out as two separate successive processes. Thus, it is possible to accelerate plasma collection without having to apply pressure on the sample during the separation process. According to the present invention, the plasma is released substantially only by means of an action on the second zone of the separation element whereby this process can be accelerated in any desired manner (e.g., by overpressure, negative pressure, or elution processes, etc.). The plasma separation step is substantially independent of this process and occurs independently of the release process and can, for example, also be accelerated by capillary forces which act inside the first zone of the separation element. However, care should be taken that acceleration of plasma separation should only occur to the extent that a reliable separation of plasma from other blood components is still ensured. In particular, processes which would cause hemolysis during plasma separation should be avoided (e.g., those which require shear forces). Consequently, the invention enables an accelerated plasma separation process without having to accept contamination of the plasma with other blood components.

In the field of modem analysis the present invention is particularly suitable for applying pure plasma to test elements that, as described, contain a complexing agent and therefore cannot themselves separate plasma within the test element due to the complexing agent.

However, an application for test elements which do not contain a complexing agent is also contemplated. Although the plasma can also be separated commercially by means of a separation layer in the test element and, consequently, the user does not have to rely on a separate plasma separation in order to use these test elements, the system according to the present invention allows a simplified test element construction in this case. Hence, the test elements only need to have a reagent layer and no longer need to be provided with a separation layer or separation fleece. This reduces, among others, the number of production steps which lowers the costs of the test elements.

Using the test elements with a separation layer or separation fleece described in the prior art as a basis, a typical embodiment of a separation element according to the present invention is constructed as a first approximation in a similar manner. Reference is, for example, made to the document DE 3130749 for a more detailed description of commercial test elements with a separation layer. The document describes a test element in which plasma is firstly separated from blood so that only plasma is transported to a reagent layer. The reagent is then used to determine an analyte in plasma. For this purpose the test element has a flat separation layer located on the base strip on which the blood sample is applied at one end. The separation layer is composed of glass fiber material which retains the blood cells near to the site of application. In contrast, blood plasma spreads in the layer in such a manner that a "plasma lake" is available in the area of the separation layer that is distant from the separation layer. A reagent layer is usually located above or below the plasma lake which can be subsequently used to determine an analyte in the plasma. Appropriate evaluation devices that are known in the prior art are used to evaluate such a test carrier.

However, a disadvantage of these analytical systems is that the so-called "plasma lake" collected in this manner can only be used on the described system. Hence, an analysis of analytes present in the plasma is only possible within the scope of the test carrier system since it is not possible to release plasma from the test carrier.

If a device according to the present invention contains a separation element which is designed like such a simplified test element, such a separation element, for example, comprises a separation layer in its first zone which is also referred to as a separation fleece in the following and it comprises a transport fleece in a second zone in which the plasma collects in an area that is distant from the separation layer. Consequently, a typical embodiment of the separation element has a test carrier-like, strip-like structure without a reagent layer being present. The separation element typically comprises a filter in its separation fleece which, for example, is composed of glass fiber material to ensure a substantially complete separation of plasma from blood. Other commercial fleeces are, for example, described in the document EP 0 045 476 or are commercially available under the name Whatman fleece. In this case, the filtering process according to the present invention is substantially not assisted by pressure to avoid destruction of blood cells in the first zone of the separation element. If, for example, negative pressure is applied to the first zone of the separation element to assist the filtration process, then care should be taken that pressure is only exerted to an extent that does not cause hemolysis.

Plasma is then subsequently released by an action on the second zone of the separation element without influencing the first zone of the separation element. Thus, according to the present invention, a contamination of the plasma by the process step of plasma release is prevented.

Pressure is typically applied to the second zone of the separation element in order to release plasma such that plasma is pressed out of the second zone of the separation element. If plasma is pressed out of the separation element care should be taken that pressure is only exerted on the second zone of the separation element in which there are no more blood components to avoid hemolysis. In principle, a variety of methods are contemplated for releasing the plasma whereby the process step of plasma release takes place according to the invention independently of the plasma separation so that the plasma separation step does not impose any constraints on the plasma release. Another example of plasma release is to elute the separated plasma. The released plasma is subsequently discharged in a dosed manner through an outlet of the device.

It has also proven to be advantageous for the release of the plasma when forces for releasing the plasma act on the second zone of the separation element substantially perpendicularly to the plane in which the separation element is located. This ensures that there is no effect on the first zone of the separation element which could otherwise contaminate the released plasma with the other blood components.

In this connection, an embodiment using a plunger is contemplated in which the plunger is arranged within the device above or below the plane in which the second zone of the separation element is located. Hence, pressing the plunger against the separation element only exerts pressure on the second zone of the separation element and thus plasma is released.

It is also contemplated that the second zone of the separation element is firstly separated from the first zone of the separation element in order to ensure the release of pure plasma so that, for example, the separation element zones can be spatially separated. In this case it is advantageous to take care that the second zone is only separated from the first zone at the site of the separation element in which substantially only plasma is present so that no corpuscular components can contaminate the plasma in the second zone of the separation element. The spatial separation now allows the plasma to be released in a variety of manners without the risk of affecting the first zone.

The second zone of the separation element can, for example, be separated from the first zone by a holder which is connected to the second zone of the separation element. If the user exerts a force (e.g., pulling, pressing, twisting, etc.) on this holder this force is directly or indirectly transferred to the second zone of the separation element and thus results in a detachment of the second zone. For example, it is possible that a rotation of the holder by typically about 90° detaches the second zone from the first zone which is fixed in a permanent position within the device.

In another embodiment, the separation element is detached and the plasma is subsequently released from the second zone in two successive steps which are carried out by actuating the same trigger unit on the device. Such a trigger unit is then linked to the holder of the device in such a manner that when the trigger unit is actuated first it initially results in a severing of the element and another actuation of the trigger unit results in plasma release. Trigger units can be in the form of a release button which in a first step, for example, causes a rotation of a holder which is connected to the second zone of the separation element resulting in a rotation of this separation element. During the rotation of the second zone attached to the holder the first part of the separation element remains in a permanent position in the device. The forces exerted by the rotation result in a severing of the separation element. In this case it is, for example, contemplated that a cutting element is positioned in the device in such a manner that the second zone of the separation element is pressed against the cutting element during the rotation. This facilitates a severing of the separation element and can be carried out precisely. If a cutting element is omitted the separation element can also be severed by tearing the first zone from the second zone. Subsequently, the plasma is released by the discharge unit.

If the separation element is designed as a single-use article in an embodiment of the device, an irreversibly severing of the element is not disadvantageous; it is also possible to offer the holder as a single-use article that is permanently connected to the separation element. This would greatly simplify the handling of the devices for the user when reinserting a new separation element since especially older persons have difficulties in handling small instrument components. Moreover, the holder and separation element can be stored in a dispenser which dispenses individual units of the single-use article.

In accordance with yet another embodiment of the present invention, a method for separating and discharging plasma is provided. The method comprises applying blood to a first zone of a separation element which comprises a first and a second zone. The plasma is separated from other blood components by the separation element during which the plasma is passed into the second zone of the separation element and the remaining blood components are substantially retained in the first zone of the separation element. Subsequently, the second zone of the separation element is processed in such a manner that plasma is released from the second zone of the separation element. In this connection, no processing of the first zone of the separation element should occur which would cause plasma to be contaminated with previously separated blood components by, for example, hemolysis. The released plasma is discharged through an outlet of the device.

Embodiments of the method of the present invention are derived as described. The method for plasma separation and discharge is typically carried out by means of the device of the present invention, as described herein.

The device according to the present invention and the method according to the present invention consequently allow a simple and rapid separation of plasma from blood on a microliter scale. The device is convenient to handle and can be manufactured economically.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings where like structure is indicated with like reference numerals and in which:

FIGS. 3a)-c) are schematic illustrations of a device for separating and discharging plasma with a rotatably pivoted holder shown in accordance with yet another embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of embodiment(s) of the present invention.

DETAILED DESCRIPTION OF THE INVENTION

Figure 1:
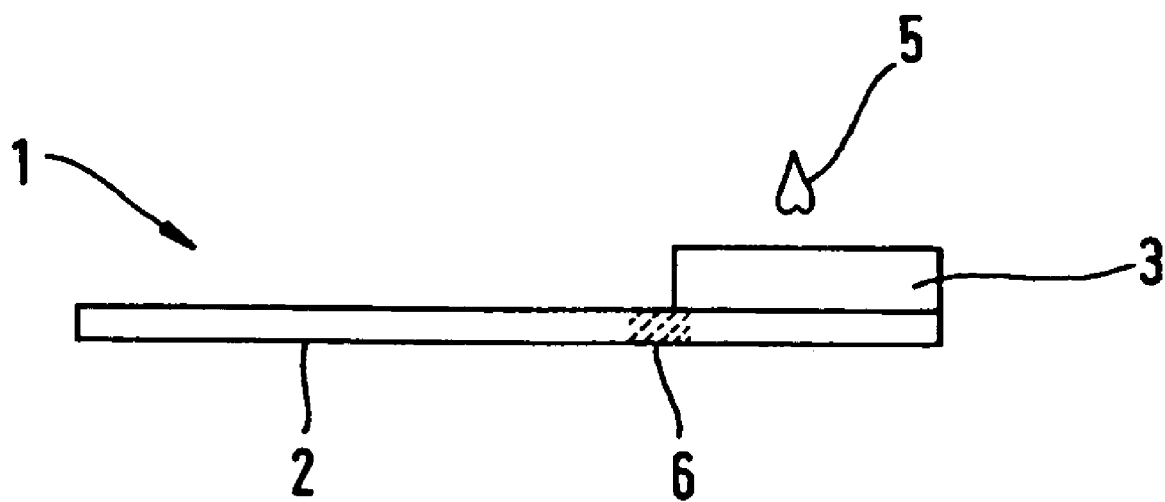
FIG. 1 is a schematic illustration of a separation element shown in accordance with one embodiment of the present invention.
Figure 2:
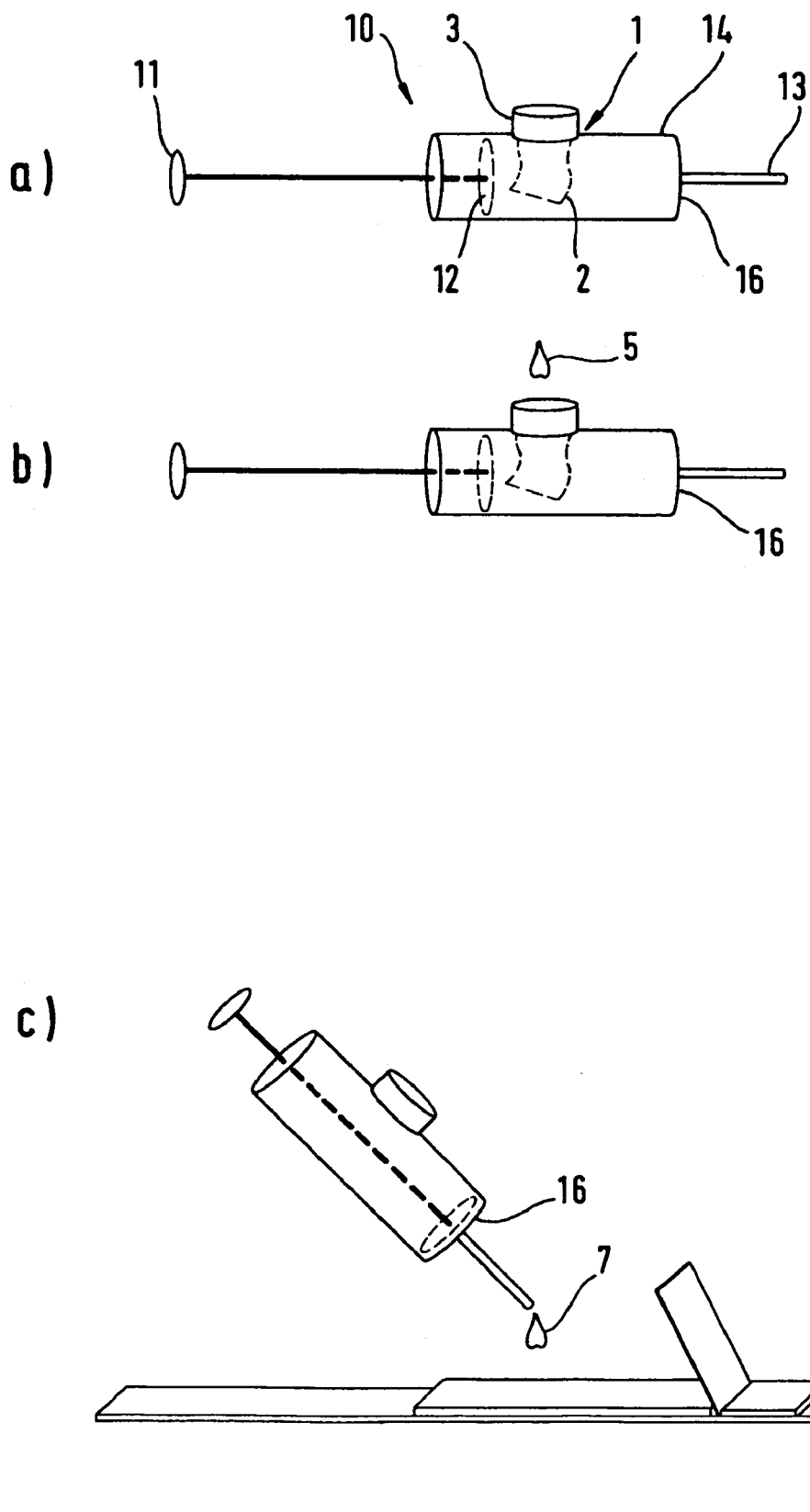
FIGS. 2a)-c) are schematic illustrations of a device for separating and discharging plasma shown in accordance with another embodiment of the present invention.

Referring initially to FIG. 1, an example of the construction of a separation element (1) in accordance with one embodiment of the present invention, is illustrated. The separation element (1) comprises a transport fleece (2) which, for example, consists of glass fibers. A separation fleece (3) which is composed of a filter medium is mounted on the transport fleece (2). The main difference between the transport and the separation fleece is their different densities. In the prior art a density of 77 g/cm$^2$ is, for example, given for a separation fleece and 53 g/cm$^2$ for a transport fleece (Whatman fleece). The smaller thickness of the transport fleece allows a rapid transport of the sample along the fleece whereas the larger thickness of the separation fleece ensures a reliable separation of plasma from blood. When a blood drop (5) is applied, the blood enters the separation fleece (3). The filter medium in the separation fleece separates the blood components from the plasma and retains them in the separation fleece (3). The plasma can be passed on by means of capillary forces which act within the transport fleece. In this case it has been often observed that small concentrations of blood components from the separation fleece (3) can enter a small area of the transport fleece (2) due to capillary forces. This area is referred to as a transition zone (6) and does not contain pure plasma. In an embodiment of the inventive device, the discharge unit therefore does not act on the transition zone of the transport fleece during release of the plasma in order to avoid contamination of the remaining plasma with impurities that are contained therein. As shown in FIG. 2, the transition zone is avoided by, for example, detaching the second zone of the test element from the first zone on the other side of this transition zone to ensure that pure plasma is obtained.

FIGS. 2a) to c) are examples of a method for plasma separation using a device (10) according to another embodiment of the present invention. The device comprises a hollow body (14) which is provided with an outlet (13). The separation element (1) is arranged within the hollow body (14) in such a manner that the separation fleece (3) protrudes from the hollow body (14) and is easily accessible for the user. The transport fleece (2) is located within the hollow body (14). The device also comprises a plunger (12) which is movably mounted within the device (14). The radius of the plunger (12) is substantially identical to the inner radius of the hollow body (14) such that the plunger (12) can be moved by means of a button (11) within the device. FIG. 2b) shows application of blood (5) on a separation fleece (3) of a separation element (1). If the blood enters the separation fleece, the plasma is passed along the separation fleece whereas the remaining blood components are retained in the separation fleece. A complete plasma separation occurs after about 2 to 10 sec. The separated plasma is now transported into the transport fleece (2). Actuation of the button (11) firstly presses the plunger (12) against the transport fleece (2) such that this area of the separation element is swept along by the plunger within the hollow body (14). Since the separation fleece (3) is permanently positioned in the hollow body, this results in a detachment of the transport fleece from the separation fleece whereby it is severed on the other side of the transition zone (6) shown in FIG. 1. Further actuation of the button (11) presses the separated transport fleece (2) against the wall (16) of the housing (14). In this process the plunger (12) presses the plasma out of the transport fleece (2) and releases it. Subsequently, plasma (7) is discharged from the outlet (13) of the device. The plasma can then, for example, be applied to a test element (17) to determine the HDL concentration.

FIG. 3 shows various views of another embodiment of the device (a-c). Compared to the embodiment shown in FIG. 2, the device additionally comprises a rotatably pivoted holder (21) in which a separation element (1) is positioned within a channel (23). The separation element (1) is positioned in the holder in such a manner that the separation fleece (3) protrudes outside the holder and device in such a manner that it is readily accessible for blood application by the user as illustrated by the side-views. The device is also provided with a plunger (12) which is connected with the button (11). Furthermore, the button (11) can operate a rotating element (22). Firstly, blood is applied to the separation fleece (3) of the separation element (1) as shown in side-view in FIG. 3a). After the plasma has been separated from blood, the rotating element (22) is operated by a first pressing of the button (11). The holder (21) is rotated by about 90° by a downwards movement of the rotating element (22). This detaches the separation fleece (3) from the transport fleece (2) during which the transition zone (6) of the transport fleece (2) remains attached to the separation fleece (3). Further actuation of the button (11) results in the plunger (12) which is firstly within a channel (23a) being transferred into the channel region (23b). This presses together the transport fleece against a sieve (24) located in the outlet (13). The sieve (24) typically has a small thickness of 20 to 300 µm in order to avoid an excessive dead volume. The plasma is discharged through the outlet (13).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A device for separating and discharging plasma comprising:
   a hollow body;
   a separation element comprising a separation fleece as a first zone and a transport fleece as a second zone, wherein
      the separation element is configured such that the first zone is accessible for blood application by a user, and
      when blood is applied to the first zone, plasma is passed into the second zone, and the remaining blood components are substantially completely retained in the first zone; and
   a plunger configured to be actuated within the hollow body, wherein upon actuation the plunger is configured to detach the second zone from the first zone and press the second zone against a wall of the hollow body to discharge the separated plasma through an outlet of the device.

2. The device of claim 1, wherein the separation element is a single-use article.

3. The device, of claim 1, wherein the first zone is positioned within the device laterally next to the second zone such that the plunger acts on the second zone of the separation element substantially perpendicular to the plane in which the separation element is located.

4. The device of claim 1 wherein the second zone is positioned in a movable holder within the device.

5. The device of claim 4, wherein the bolder is configured to rotate about 90° resulting in a detachment of the second zone from the first zone.

6. The device of claim 1, wherein the second zone is configured to detach from the first zone and the detachment and release of plasma from the second zone occur in two consecutive steps by actuating a button on the plunger.

7. The device of claim 1, wherein the separation element is strip-shaped.

8. A system for detecting analytes in blood comprising:
   a hollow body;
   a separation element comprising a separation fleece as a first zone and a transport fleece as a second zone, wherein
      the separation element is configured such that the first zone is accessible for blood application by a user, and
      when blood is applied to the first zone, plasma is passed into the second zone, and the remaining blood components are substantially completely retained in the first zone;
   a plunger configured to be actuated within the hollow body, wherein upon actuation the plunger is configured to detach the second zone from the first zone and press the second zone against a wall of the hollow body to discharge the separated plasma through an outlet of the device; and
   a test element that enables detection of an analyte in plasma when the separated plasma is applied.

9. The system of claim 8, wherein the structure of the test element is simplified such that there is no plasma separation by the test element itself.

10. A method for plasma separation and discharge comprising:
    providing a device comprising;
       a hollow body,
       a separation element comprising a separation fleece as a first zone and a transport fleece as a second zone, and
       a plunger be actuated within the hollow body;
    applying blood to the first zone of the separation element;
    separating plasma from other blood components by means of the separation element, the blood components being substantially retained in the first zone and the plasma being passed into the second zone of the separation element,
    actuating the plunger to detach the second zone from the first zone and press the second zone against a wall of the hollow body; and discharging the separated plasma through an outlet.

11. The method of claim 10 further comprising eluting the separated plasma from the second zone.

12. The method of claim 10 further comprising separating the plasma by filtering.

13. The method of claim 10 further comprising detecting at least one analyte in the blood.

14. The method of claim 10, wherein the applied blood volume is between about 30 µl and about 150 µl.

15. The method of claim 13, wherein the at least one analyte is high density lipoproteins.

* * * * *